US008440877B2

(12) United States Patent
Collins et al.

(10) Patent No.: US 8,440,877 B2
(45) Date of Patent: May 14, 2013

(54) ALIGNMENT AIDS FOR A SENSING ARTICLE

(75) Inventors: Meghan E. Collins, Lakemoor, IL (US); Thomas M. Ales, III, Neenah, WI (US); Shirlee A. Weber, Neenah, WI (US); Andrew M. Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1221 days.

(21) Appl. No.: 11/444,847

(22) Filed: May 31, 2006

(65) Prior Publication Data
US 2007/0282286 A1 Dec. 6, 2007

(51) Int. Cl.
*A61F 13/15* (2006.01)
*A61F 13/20* (2006.01)

(52) U.S. Cl.
USPC ..................... 604/361; 604/385.01

(58) Field of Classification Search ............... 604/358, 604/385.01, 385.22–385.24, 385.27, 361–362, 604/367, 378
See application file for complete search history.

(56) References Cited

U.S. PATENT DOCUMENTS

| | | | |
|---|---|---|---|
| 3,961,112 A | 6/1976 | Genevitz et al. | |
| 4,334,530 A | 6/1982 | Hassell | |
| 4,662,875 A | 5/1987 | Hirotsu et al. | |
| 4,704,116 A | 11/1987 | Enloe | |
| 4,768,023 A | 8/1988 | Xie | |
| 4,798,603 A | 1/1989 | Meyer et al. | |
| 4,940,464 A | 7/1990 | Van Gompel et al. | |
| 5,019,070 A | 5/1991 | Ruben | |
| 5,133,707 A | 7/1992 | Rogers et al. | |
| 5,176,672 A | 1/1993 | Bruemmer et al. | |
| 5,264,830 A | 11/1993 | Kline et al. | |
| 5,275,588 A | 1/1994 | Matsumoto et al. | |
| 5,392,032 A * | 2/1995 | Kline et al. ................ | 340/604 |
| 5,469,145 A | 11/1995 | Johnson | |
| 5,486,166 A | 1/1996 | Bishop et al. | |
| 5,490,846 A | 2/1996 | Ellis et al. | |
| 5,509,915 A | 4/1996 | Hanson et al. | |
| 5,531,731 A | 7/1996 | Brusky | |
| 5,560,798 A | 10/1996 | Brusky | |
| 5,760,694 A * | 6/1998 | Nissim et al. ............... | 340/604 |
| 5,766,389 A | 6/1998 | Brandon et al. | |
| 5,808,554 A | 9/1998 | Shuminov | |
| 5,820,973 A | 10/1998 | Dodge, II et al. | |
| 5,838,240 A * | 11/1998 | Johnson ..................... | 340/604 |
| 5,897,546 A | 4/1999 | Kido et al. | |

(Continued)

FOREIGN PATENT DOCUMENTS

| | | |
|---|---|---|
| EP | 0 440 163 B1 | 4/1995 |
| EP | 0 570 980 B1 | 7/1997 |

(Continued)

*Primary Examiner* — Michele M Kidwell
(74) *Attorney, Agent, or Firm* — Randall W. Fieldhack; David J. Arteman; R. Joseph Foster, III

(57) ABSTRACT

Presented is a sensing absorbent article system including an absorbent article having a liner and an outer cover, the absorbent article including a sensing means, an article design scheme, and an attachment zone having an attachment zone design scheme, wherein the attachment zone design scheme is visually differentiable from the article design scheme. Also presented is a sensing absorbent article system including an absorbent article having a liner and an outer cover, the absorbent article including a sensing means, an article design scheme, and an attachment zone adapted to indicate the proper position for a signaling device.

9 Claims, 11 Drawing Sheets

U.S. PATENT DOCUMENTS

| | | | |
|---|---|---|---|
| 5,908,411 | A | 6/1999 | Matsunari |
| 5,993,433 | A | 11/1999 | St. Louis et al. |
| 6,045,543 | A | 4/2000 | Pozniak et al. |
| 6,200,250 | B1 | 3/2001 | Janszen |
| 6,246,330 | B1 | 6/2001 | Nielsen |
| 6,248,097 | B1 | 6/2001 | Beitz et al. |
| 6,352,528 | B1 | 3/2002 | Weber et al. |
| 6,417,455 | B1 | 7/2002 | Zein et al. |
| 6,645,190 | B1 | 11/2003 | Olson et al. |
| 6,658,432 | B1 | 12/2003 | Alavi et al. |
| 8,733,483 | | 5/2004 | Raufman et al. |
| 6,791,004 | B2 | 9/2004 | Sprengard et al. |
| 7,394,391 | B2 * | 7/2008 | Long ............................ 340/573.5 |
| 2001/0021833 | A1 | 9/2001 | Schmidt et al. |
| 2002/0070868 | A1 | 6/2002 | Jeutter et al. |
| 2003/0106825 | A1 * | 6/2003 | Molina et al. ................. 206/494 |
| 2004/0087922 | A1 * | 5/2004 | Bobadilla ...................... 604/361 |
| 2004/0097896 | A1 | 5/2004 | Raufman et al. |
| 2004/0147888 | A1 | 7/2004 | Huang et al. |
| 2004/0220538 | A1 | 11/2004 | Panopoulos |
| 2005/0137542 | A1 * | 6/2005 | Underhill et al. .............. 604/361 |

FOREIGN PATENT DOCUMENTS

| | | |
|---|---|---|
| EP | 1 038 511 A1 | 9/2000 |
| EP | 0 756 855 B1 | 11/2000 |
| WO | WO 99/22688 A1 | 5/1999 |
| WO | WO 00/35401 A1 | 6/2000 |
| WO | WO 00/37009 A2 | 6/2000 |
| WO | WO 01/21126 A1 | 3/2001 |
| WO | WO 02/041819 A1 | 5/2002 |
| WO | WO 02/49561 A1 | 6/2002 |
| WO | WO 02/049568 A1 | 6/2002 |

* cited by examiner

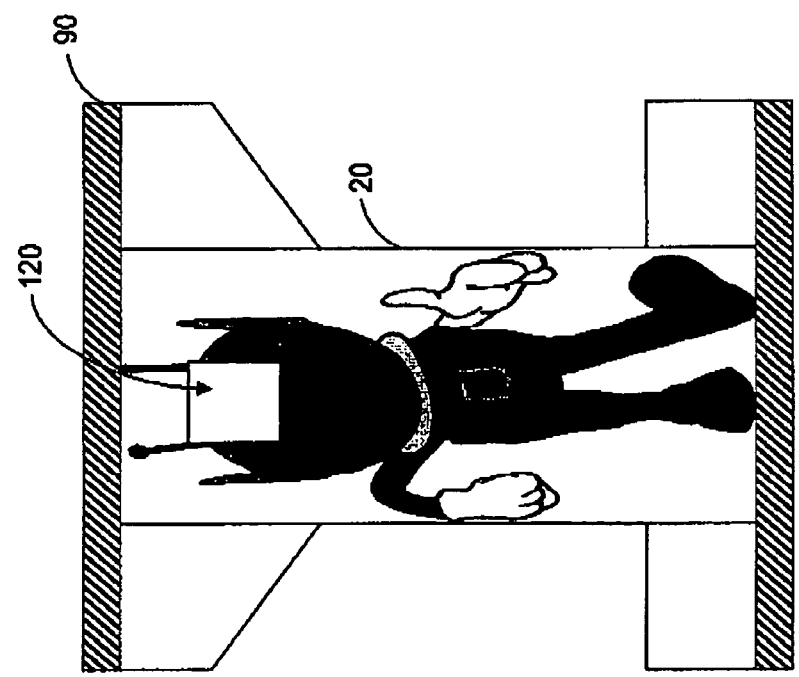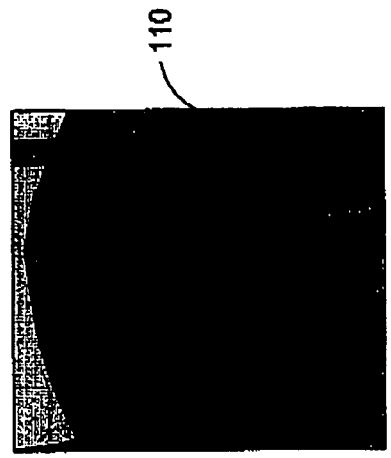

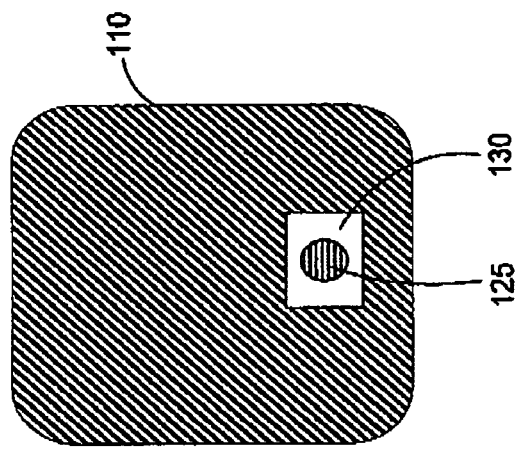
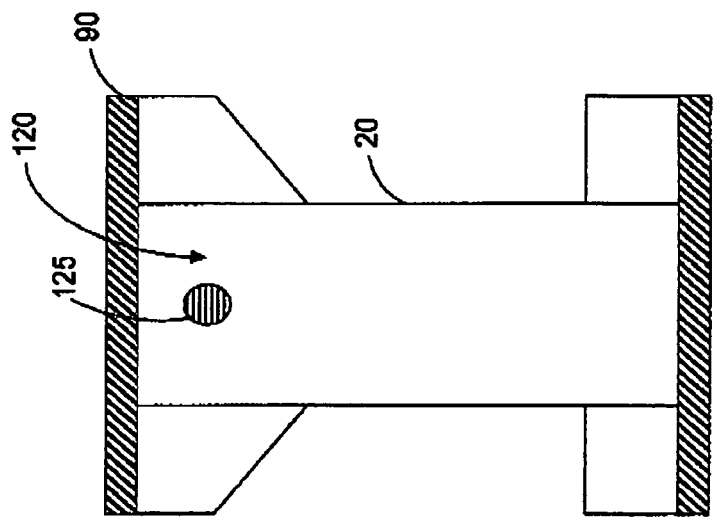

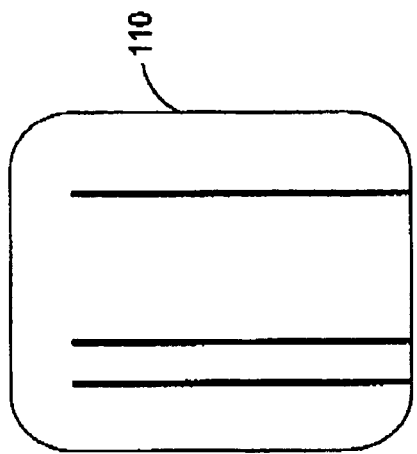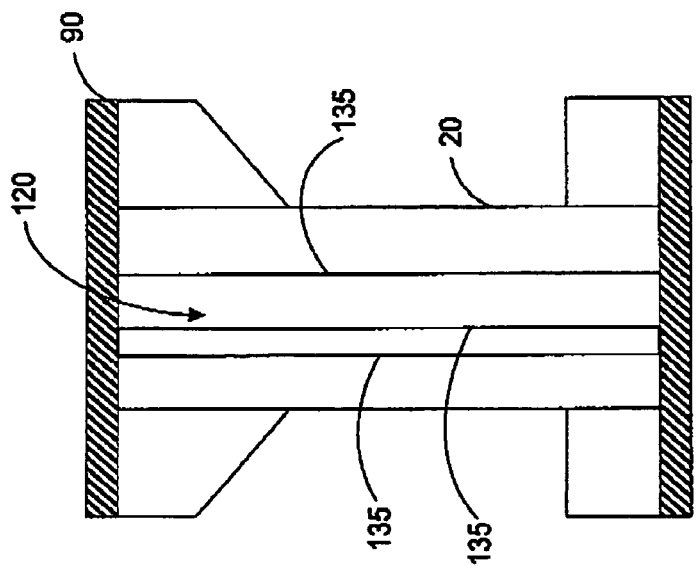

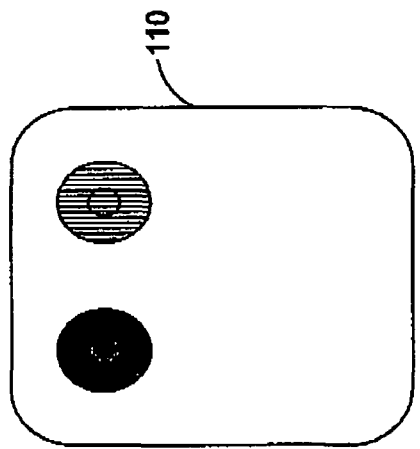
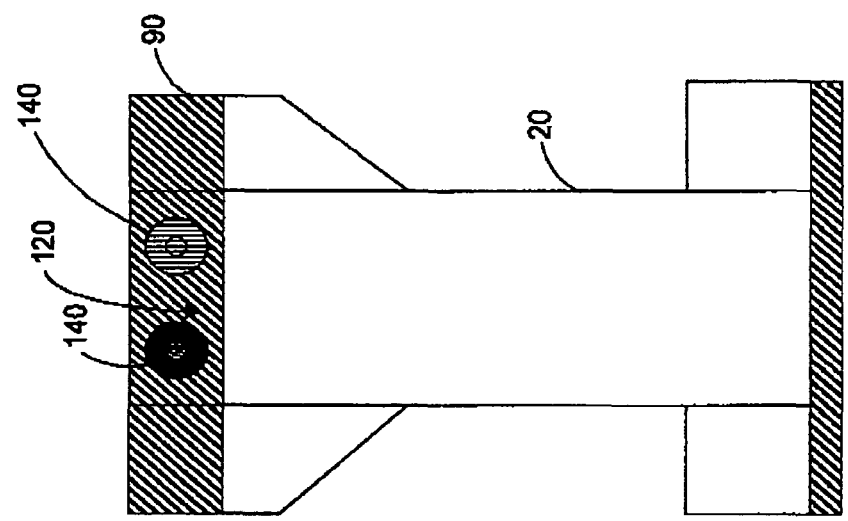

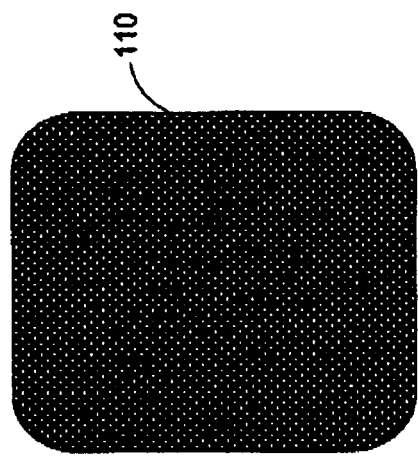
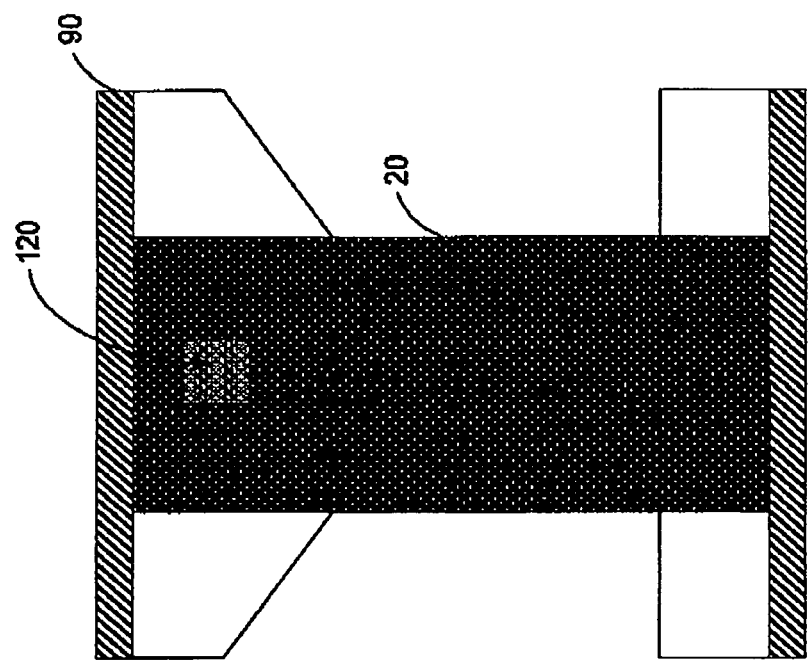
FIG. 9b
FIG. 9a

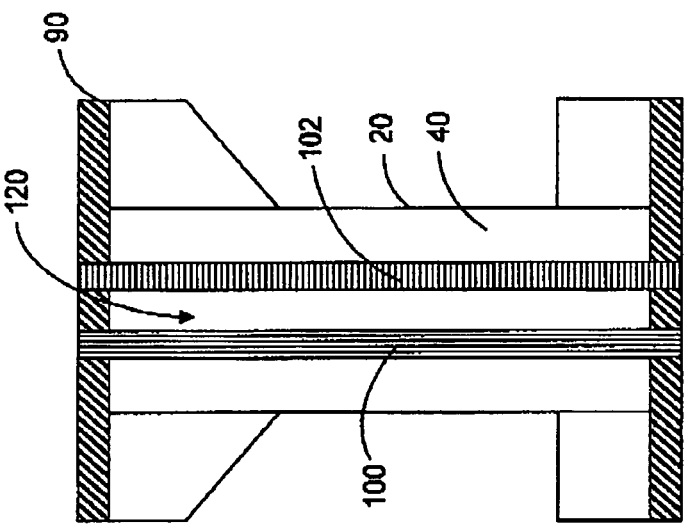
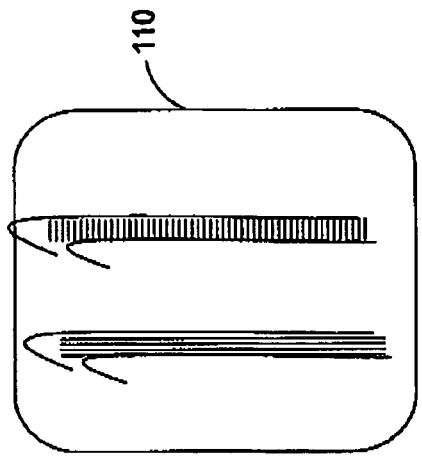
FIG. 10a
FIG. 10b

ALIGNMENT AIDS FOR A SENSING ARTICLE

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

Many absorbent articles have been adapted for use in a training program, such as toilet training or enuresis control, or to provide indication of various medical, physical, or other conditions. Accordingly, various types of sensors and indicators, including moisture or wetness indicators, have been suggested for use in absorbent articles. Wetness indicators, for example, may include alarm devices that are designed to assist parents or attendants to identify a wet diaper condition quickly upon insult. The devices produce either a visual or an audible signal.

In some aspects of the present invention, for instance, inexpensive conductive threads or foils have been placed in the absorbent articles. The conductive materials serve as conductive leads for a signaling device and form an open circuit in the article that can be closed when a body fluid, such as urine, closes the circuit. In other aspects of the present invention, various other sensors have been included in absorbent articles, where the sensors may communicate test results, indications, or other data to a user or a caregiver via a signaling device. In these aspects of the present invention, although the absorbent articles may be disposable, the signaling devices are not. Thus, the signaling devices are intended to be removed from the article and reattached to a subsequent article.

Problems, however, have been encountered in using such articles for training and/or notification purposes in that executions of the concept are very limited in their convenience and efficacy, which translate to a loss in benefit to the consumer. Use of such articles and signaling devices, including transferring signaling devices between articles, in a hectic medical, institutional, or home setting can be difficult, especially where proper alignment of the signaling device with the absorbent article is essential.

SUMMARY OF THE INVENTION

As caregivers undertake training, indication, and/or notification programs to address toilet training, enuresis control, incontinence monitoring, or condition monitoring, which apply across demographics, those caregivers would benefit by gaining greater access to products that are specifically designed to enhance the convenience, interest, and enjoyment of the products and thus the effectiveness of such programs.

The invention described herein solves the problems described above and provides an increase in convenience and efficacy in using wetness and other sensors in absorbent articles by increasing the convenience with which the sensing components may be combined. In general, the present disclosure is directed to sensing absorbent articles with easy-to-use signaling devices. The signaling device, for instance, may be configured to indicate to a user that a body fluid is present in the sensing absorbent article.

For example, in one aspect of the present invention, the invention includes a sensing absorbent article system including an absorbent article having a liner and an outer cover, the absorbent article including a sensing means, an article design scheme, and an attachment zone having an attachment zone design scheme, wherein the attachment zone design scheme is visually differentiable from the article design scheme.

In another aspect of the present invention, the invention includes a sensing absorbent article system including an absorbent article having a liner and an outer cover, the absorbent article including a sensing means, an article design scheme, and an attachment zone adapted to indicate the proper position for a signaling device.

In another aspect of the present invention, the invention includes a sensing absorbent article system including an absorbent article having a liner and an outer cover, the absorbent article including a portion of a visual characteristic; and a signaling device adapted to connect with the absorbent article, the signaling device having another portion of the visual characteristic, wherein signaling device when properly aligned with the absorbent articles forms a complete visual characteristic.

In another aspect of the present invention, the invention includes an absorbent article including a sensing component; a liner; and an outer cover, wherein the outer cover includes a visual characteristic, and wherein a portion of the visual characteristic is missing.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

FIGS. 3a and 3b are schematic plan views of one aspect of the absorbent article illustrated in FIG. 1;

FIGS. 6a and 6b are schematic plan views of one aspect of the absorbent article illustrated in FIG. 1;

FIGS. 7a and 7b are schematic plan views of one aspect of the absorbent article illustrated in FIG. 1;

FIGS. 8a and 8b are schematic plan views of one aspect of the absorbent article illustrated in FIG. 1;

FIGS. 9a and 9b are schematic plan views of one aspect of the absorbent article illustrated in FIG. 1; and FIGS. 10a and 10b are schematic plan views of one aspect of the absorbent article illustrated in FIG. 1;

Figure 1:
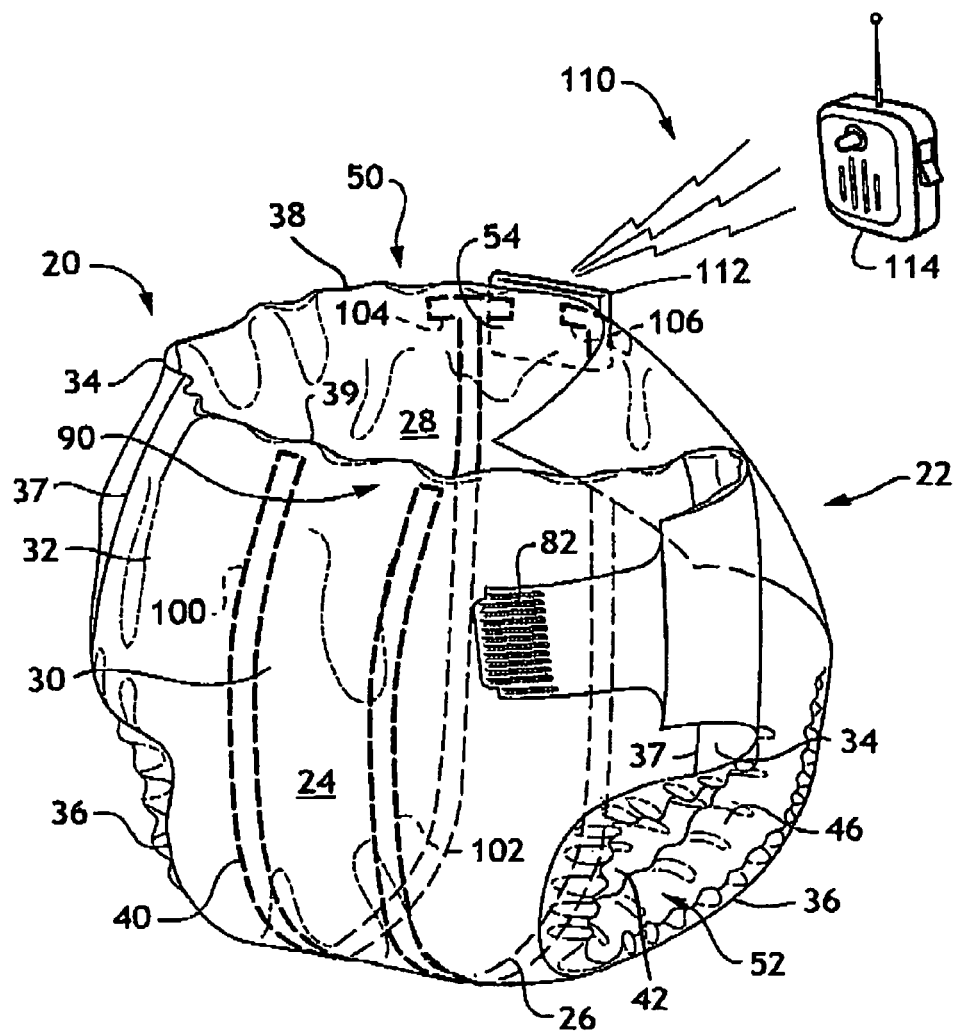
FIG. 1 perspective view of an absorbent article of the present invention.
Figure 2B:
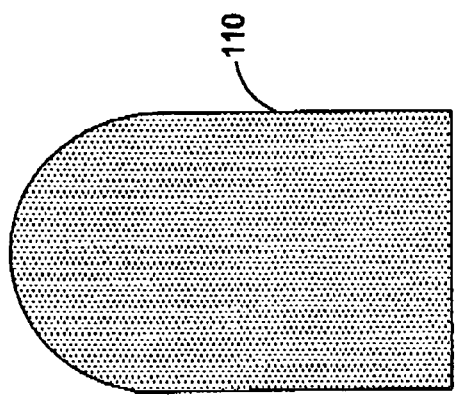
FIGS. 2a and 2b are schematic plan views of one aspect of the absorbent article illustrated in FIG. 1.
Figure 2A:
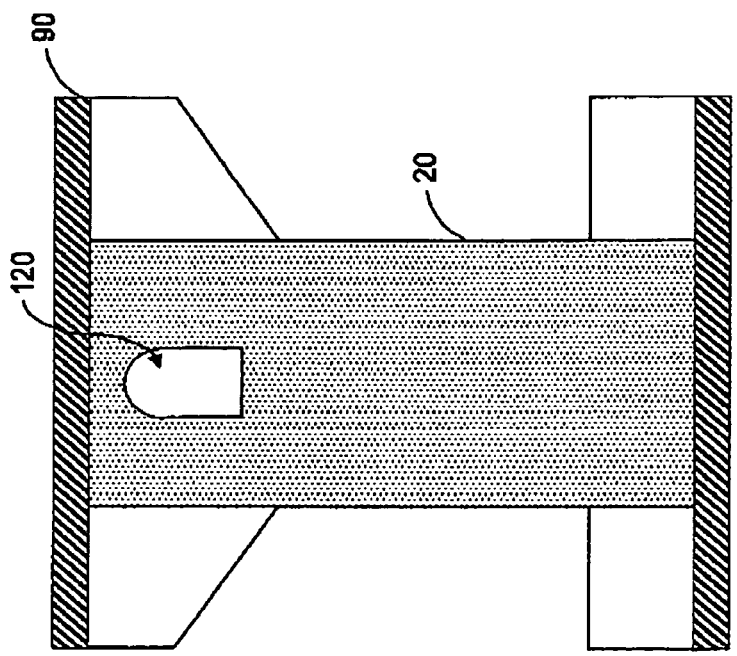

Repeat use of reference characters in the present specification and drawings is intended to represent the same or analogous features or elements of the present invention. The drawings are representational and are not necessarily drawn to scale. Certain proportions thereof may be exaggerated, while others may be minimized.

DETAILED DESCRIPTION OF THE INVENTION

It is to be understood by one of ordinary skill in the art that the present discussion is a description of exemplary aspects of the present invention only, and is not intended as limiting the broader aspects of the present invention.

The present disclosure is generally directed to sensing absorbent articles adapted to be attached to a signaling device that may be configured to indicate the presence of a body fluid in the absorbent article or other changes in the condition of the product or wearer. The absorbent article may be, for instance, a diaper, a training pant, a pre-fastened pant, a swimming pant, an incontinence product, a feminine hygiene product, a medical garment, a bandage, or any other suitable article.

The invention described herein may be used with any type of sensing article. In one type of sensing article used as a non-limiting example herein, wetness sensing absorbent articles may include an open circuit that becomes closed when a conductive fluid, such as a body fluid, is present in between a pair of conductive leads. Alternatively, wetness sensing absorbent articles may include a closed circuit that becomes open when a fluid, such as a body fluid, is present. Generally, the wetness sensing absorbent articles containing the circuit are disposable meaning that they are designed to be discarded after a limited use rather than being laundered or otherwise restored for reuse.

The circuit contained within the wetness sensing absorbent articles of the present disclosure is configured to be attached to a signaling device. The signaling device can provide power to the circuit while also including some type of audible, visible and/or electromagnetic signal that indicates to the user the presence of a body fluid. Although the wetness sensing absorbent article may itself be disposable, the signaling device may be reusable from article to article. In this regard, the present disclosure is particularly directed to different types of attachment mechanisms that allow easy connection between the circuit in the wetness sensing absorbent article and the signaling device.

As described above, the circuit in combination with the signaling device may be configured to indicate the presence of a body fluid contained within the wetness sensing absorbent article. The particular targeted body fluid may vary depending upon the particular type of wetness sensing absorbent article and the desired application. For instance, in one aspect of the present invention, the wetness sensing absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine or menses, such as a polysaccharide.

Referring to FIG. 1, for non-limiting exemplary purposes, a wetness sensing absorbent article 20 is shown. The wetness sensing absorbent article 20 may or may not be disposable. It is understood that the present invention is suitable for use with various other wetness sensing absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing wetness sensing absorbent articles such as the wetness sensing absorbent article 20 of the various aspects of the present invention are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

A wetness sensing absorbent article 20 is representatively illustrated in FIG. 1 in a partially fastened condition.

The wetness sensing absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The wetness sensing absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the wetness sensing absorbent article 20, which when worn, wholly or partially cover or encircle the waist or mid-lower torso of the wearer. The crotch region 26 generally is that portion of the wetness sensing absorbent article 20 which, when worn, is positioned between the legs of the wearer and covers the lower torso and crotch of the wearer. The wetness sensing absorbent article 20 has a pair of laterally opposite side edges 36 and a pair of longitudinally opposite waist edges, respectively designated front waist edge 38 and back waist edge 39.

The illustrated wetness sensing absorbent article 20 includes a chassis 32 that, in this aspect of the present invention, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The liner 42 can be generally adapted, i.e., positioned relative to the other components of the article 20, to be disposed toward the wearer's skin during wear of the wetness sensing absorbent article. The chassis 32 may further include an absorbent structure (not shown) disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the wetness sensing absorbent article 20 may also suitably include leg elastic members (not shown), as are known to those skilled in the art.

In some aspects of the present invention, the wetness sensing absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 1, the wetness sensing absorbent article 20 further includes a pair of opposing elastic side panels 34 that are attached to the back region of the chassis 32. As shown particularly in FIG. 1, the side panels 34 may be stretched around the waist and/or hips of a wearer to secure the garment in place. The elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques. Ultimately, the side panels 34 are generally aligned with a waist region 90 of the chassis.

In an alternative aspect of the present invention, the elastic side panels may also be integrally formed with the chassis 32. For instance, the side panels 34 may comprise an extension of the bodyside liner 42, of the outer cover 40, or of both the bodyside liner 42 and the outer cover 40.

The side panels 34 are connected to the back region of the wetness sensing absorbent article 20 and extend over the front region of the article when securing the article in place on a user. It should be understood, however, that the side panels 34 may alternatively be connected to the front region of the article 20 and extend over the back region when the article is donned.

With the wetness sensing absorbent article 20 in the fastened position as partially illustrated in FIG. 1, the elastic side panels 34 may be connected by a fastening system 82 to define a 3-dimensional wetness sensing absorbent article configuration having a waist opening 50 and a pair of leg openings 52. The waist opening 50 of the article 20 is defined by the waist edges 38 and 39 which encircle the waist of the wearer.

In the aspects of the present invention shown in the figures, the side panels are releasably attachable to the front region 22 of the article 20 by the fastening system 82. It should be understood, however, that in other aspects of the present invention the side panels may be permanently joined to the chassis 32 at each end. The side panels may be permanently bonded together, for instance, when forming a training pant or absorbent swimwear.

The fastening system 82 may include laterally opposite first fastening components adapted for refastenable engagement to corresponding second fastening components. The fastening system 82 may include any refastenable fasteners suitable for wetness sensing absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In addition to possibly having elastic side panels, the wetness sensing absorbent article 20 may include various waist elastic members for providing elasticity around the waist opening. For example, as shown in the figures, the wetness sensing absorbent article 20 can include a front waist elastic member 54 and/or a back waist elastic member (not shown).

As described above, the present disclosure is particularly directed to incorporating a body fluid indicating system. One such system is described below. Other systems include a wetness liner such as that described in U.S. Pat. No. 6,658,432 to Underhill et al., a temperature system, a system in which graphics fade or appear, and any other suitable body fluid indicating system. One such body fluid indicating system is the wetness indicating system described herein. In this regard, as shown in FIG. 1, the wetness sensing absorbent article 20 includes a first conductive element 100 spaced from a second conductive element 102. In this aspect of the present invention, the conductive elements extend from the front region 22 of the wetness sensing absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002 to Zein et al. The first conductive element 100 may not intersect the second conductive element 102 in order to form an open circuit that may be closed, for instance, when a conductive fluid is positioned in between the conductive elements. In other aspects of the present invention, however, the first conductive element 100 and the second conductive element 102 may be connected to a sensor within the chassis. The sensor may be used to sense changes in temperature or may be used to sense the presence of a particular substance, such as a metabolite.

In the aspect of the present invention shown in FIG. 1, the conductive elements 100 and 102 extend the entire length of the wetness sensing absorbent article 20. It should be understood, however, that in other aspects of the present invention the conductive elements may extend only to the crotch region 26 or may extend to any particular place in the wetness sensing absorbent article where a body fluid is intended to be sensed.

The conductive elements 100 and 102 may be incorporated into the chassis 32 at any suitable location as long as the conductive elements are positioned so as to contact a body fluid that is absorbed by the wetness sensing absorbent article 20. In this regard, the conductive elements 100 and 102 generally lie inside the outer cover 40. In fact, in one aspect of the present invention, the conductive elements 100 and 102 may be attached or laminated to the inside surface of the outer cover 40 that faces the absorbent structure. Alternatively, however, the conductive elements 100 and 102 may be positioned on the absorbent structure or positioned on the liner 42.

The conductive element 100 and 102 may be connected directly to a signaling device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a signaling device that is intended to be installed on the chassis by the consumer or manufacturer. The pad members 104 and 106 may create a zone for connecting the signaling device and the conductive leads or elements.

The conductive pad members 104 and 106 may have a relatively large surface area in relation to the conductive elements 100 and 102. For example, the conductive pad members 104 and 106 may have a surface area of at least 0.5 cm$^2$, at least 1 cm$^2$, at least 2 cm$^2$, and, in another aspect of the present invention, at least 3 cm². For instance, in another aspect of the present invention, the surface area of each pad member may be from about 2 cm² to about 4 cm².

The position of the conductive pad members 104 and 106 on the wetness sensing absorbent article 20 can vary depending upon where it is desired to mount the signaling device. For instance, in FIG. 1, the conductive pad members 104 and 106 are positioned in the front region 22 along the waist opening of the article. In another aspect of the present invention that is not shown, the conductive pad members 104 and 106 are positioned in the back region 24 along the waist opening of the article. It should be appreciated, however, that in other aspects of the present invention, the wetness sensing absorbent article 20 may include conductive pad members being positioned at each end of each conductive element 100 and 102. In still other aspects of the present invention, it should be understood that the pad members may be located along the side of the article or towards the crotch region of the article.

The position of the conductive pad members 104 and 106 within the multiple layers of the chassis 32 may also vary depending upon where it is desired to connect the signaling device and the type of attachment mechanism used to make a connection with the signaling device. As described above, the pad members 104 and 106 are electrically connected to the conductive elements 100 and 102. Thus, in one aspect of the present invention, the pad members 104 and 106 are positioned below (toward the body side) at least one layer of the outer cover 40. Positioning the pad members 104 and 106 below at least one layer of material may provide various advantages in some aspects of the present invention. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the wetness sensing absorbent article 20 at high machine speeds.

It should be understood, however, that in other aspects of the present invention the conductive pad members 104 and 106 may be positioned at an exterior surface of the chassis 32. For instance, the pad members 104 and 106 may be positioned on the outside surface or on the inside surface as desired.

Further details related to the structure, features, and materials of the absorbent article 20 may be found in co-pending and co-assigned U.S. patent application Ser. No. 11/414,032, filed on Apr. 27, 2006 by Allen, et al. and titled "An Array of Wetness Sensing Articles"; which is incorporated herein by reference to the extent it is consistent (i.e., not in conflict) herewith.

Referring to FIG. 1 for exemplary purposes, a signaling device 110 (as depicted by ref. numerals 112 and 114) is shown attached to the conductive pad members 104 and 106. As shown, in this aspect of the present invention, the signaling device generally 110 includes a transmitter 112 and a receiver 114. The transmitter 112 includes a pair of opposing terminals that are electrically connected to the corresponding conductive elements. When a body fluid is present in the wetness sensing absorbent article 20, the open circuit formed by the conductive elements 100 and 102 is closed which, in turn, activates the signaling device 110. In particular, in this aspect of the present invention, the transmitter 112 sends a wireless signal to the receiver 114 which then indicates to a user that a body fluid is present in the wetness sensing absorbent article 20. In other various aspects of the present invention, any chemical or physical reaction that can change conductivity can also be sensed by this type of system—examples include conductivity changes associated with electrochemical sensors inside of the absorbent article 20 such as those described in co-pending and co-assigned U.S. patent application Ser. No. 11/314,438, filed on Dec. 21, 2005 by Ales, et al. and titled "Personal Care Products with Microchemical Sensors for Odor Detection"; which is incorporated herein by reference to the extent it is consistent (i.e., not in conflict) herewith.

The signaling device 110 can emit an audible signal or a visual signal to indicate to the user that the circuit has been closed. The audible signal, for instance, may be as simple as one or more beeps to perhaps emitting a musical tune. Similarly, if the signaling device 110 issues a visible signal, the visible signal may comprise one light, a few lights, or an interactive display. In still another aspect of the present invention, the receiver 114 of the signaling device 110 may be configured to vibrate when the circuit within the wetness sensing absorbent article is closed.

In the aspect of the present invention shown in FIG. 1, the signaling device 110 includes a transmitter 112 in combination with a receiver 114. It should also be understood, however, that the signaling device may comprise a single unit that remains attached to the wetness sensing absorbent article 20. For example, the signaling device may be mounted on the wetness sensing absorbent article and issue a visible signal and/or an audible signal from the article itself.

In various aspects of the present invention, the wetness sensing absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the wetness sensing absorbent article may also include other wetness sensing features such as fading ink, appearing ink, a wetness liner, or a cooling component.

The wetness sensing absorbent article 20 may be a part of a wetness sensing system such as those described in above-referenced co-pending and co-assigned U.S. patent application Ser. No. 11/414,032, filed on Apr. 27, 2006 by Allen, et al. and titled "An Array of Wetness Sensing Articles."

One way of enhancing the convenience of a sensing article is to provide assistance in attaching a signaling device 110 to an absorbent article 20. Such assistance may be provided in the form of an alignment aid to help a user ensure that the signaling device 110 is properly positioned on the absorbent device 20, thus providing confidence that the signaling device 110 is properly attached to the absorbent article 20. As a result, the signaling device 110 can be easily aligned both vertically and horizontally. Exemplary alignment aids are discussed in more detail below.

To add convenience and thus increase the efficacy of using the absorbent article 20, the absorbent article 20 may be provided with an article design scheme. The article design scheme refers primarily to the design of the absorbent article 20, including its visual characteristics such as its shape, its coloring, and the graphics associated with it. In one aspect of the present invention, the article design scheme is primarily associated with the outer cover 40, as illustrated in FIGS. 1a-6b, 9a and 9b. In another aspect of the present invention, the article design scheme is associated with the actual attachment mechanism on the absorbent article 20, as shown in FIGS. 8a and 8b. In still another aspect of the present invention, the article design scheme is associated with the conductors inside the absorbent article 20, as shown in FIGS. 10*a* and 10*b*. The article design scheme may be associated with a character, a story, an action, an event, or any other suitable subject matter. If a character, article design schemes include a fictional character, a non-fictional character, and an animated character such as a cartoon character. If an event, article design schemes include events such as toilet training and entering school. For example, an article design scheme may be a cartoon character, where the graphics placed on the absorbent article 20 relate to that cartoon character. Graphics may be depicted on the absorbent article 20 by printing or by any other suitable means.

The absorbent article 20 also includes an attachment zone 120, as illustrated in FIGS. 2*a*-10*b*. The attachment zone 120 is the location at which the signaling device 110 is properly positioned to be attached to the absorbent article 20. In one aspect of the present invention, the attachment zone 120 is located on the outer cover 40. In a more preferred aspect of the present invention, the attachment zone 120 is located on the outer cover 40 in the back region 24 of the absorbent article 20. The attachment zone 120 may be provided with an attachment zone design scheme. The attachment zone design scheme refers primarily to the design of the attachment zone 120, including its visual characteristics such as its shape, its coloring, and the graphics associated with it. The attachment zone design scheme may be associated with a character, a story, an action, an event, or any other suitable subject matter. If a character, attachment zone design schemes include a fictional character, a non-fictional character, and an animated character such as a cartoon character. If an event, attachment zone design schemes include events such as toilet training and entering school. For example, an attachment zone design scheme may be a cartoon character, where the graphics placed on the attachment zone 120 relate to that cartoon character. Graphics may be depicted on the attachment zone 120 by printing or by any other suitable means.

In one aspect of the present invention, the attachment zone 120 is visually differentiable from the article design scheme to assist a user in properly positioning a signaling device 110 for attachment to the absorbent article 20. In various aspects of the present invention, the signaling device may be larger than, smaller than, or generally equivalent in size to that of the attachment zone 120.

In another aspect of the present invention, the attachment zone 120 may be absent of graphics. In an example illustrated in FIGS. 2*a*-3*b*, the attachment zone 120 is simply a gap in or a missing piece of the article design scheme to assist the user in properly aligning the signaling device 110 on the absorbent article 20. In still another aspect of the present invention, the attachment zone 120 may include text. In an example illustrated in FIGS. 4*a* and 4*b*, the words "Place Alarm Here" assist the user in properly aligning the signaling device 110 on the absorbent article 20.

To add further convenience and thus increase the efficacy of using the absorbent article 20, the signaling device 110 may be provided with a signaling device design scheme. The signaling device design scheme refers primarily to the design of the signaling device 110, including its visual and other characteristics such as its shape, its coloring, the sound or sounds it produces, the other signals it produces, and the graphics associated with it. The signaling device design scheme may be associated with a character, a story, an action, an event, or any other suitable subject matter, such as those described above with respect to the article design scheme. For example, a signaling device design scheme may be a cartoon character, where one or more of the graphics placed on the signaling device 110, the shape of the signaling device 110, the sound or sounds played by the signaling device 110, and the other signals produced by the signaling device 110 relate to that cartoon character. In various aspects of the present invention, the sound or sounds played by the signaling device 110 include music, sound effects, and speech. In various aspects of the present invention, the signaling device 110 may play a plurality of sounds. Graphics may be depicted on the signaling device 110 by printing, embossing, engraving, or by any other suitable means.

The signaling device 110 has a size and shape that can vary based upon the needs of the manufacturer and/or user, and on the preferences selected for the signaling device design scheme. The signaling device 110 may be any size that is suitable to contain the functional components of the signaling device 110 and/or suitable to meet the requirements of the signaling device design scheme. Similarly, the signaling device 110 may be any shape that is suitable to contain the functional components of the signaling device 110 and/or suitable to meet the requirements of the signaling device design scheme.

In one aspect of the present invention, the attachment zone 120 is sized to match the size of the signaling device 110 to provide a clear indication to the user with respect to properly positioning the signaling device 110. In another aspect of the present invention, the attachment zone 120 is shaped to match the shape of the signaling device 110 to provide a clear indication to the user with respect to properly positioning the signaling device 110. In other aspects of the present invention, the attachment zone 120 may be matched in shape to but different in size from those of the signaling device 110, or the attachment zone 120 may be matched in size to but different in shape from those of the signaling device 110 while still providing a clear indication to the user with respect to properly positioning the signaling device 110. In an example not shown, the attachment zone 120 may be as simple as a line or a rectangle printed on the outer cover 40 to match an edge or edges of the signaling device 110.

Figure 5B:
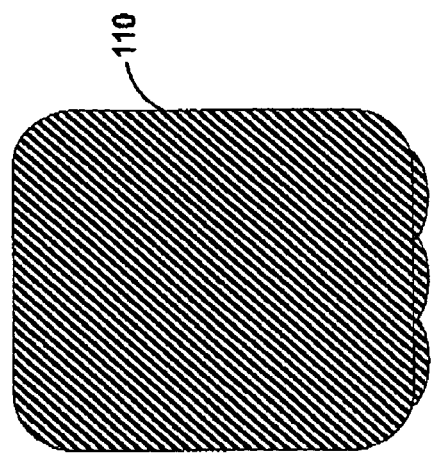
FIGS. 5a and 5b are schematic plan views of one aspect of the absorbent article illustrated in FIG. 1.
Figure 5A:
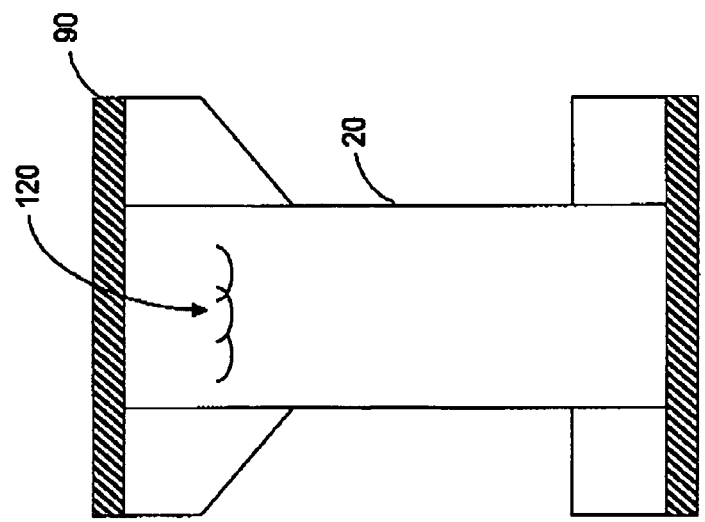

In a related aspect of the present invention, the attachment zone 120 may be a simple line or graphic representing a portion of the signaling device 110 or signaling device design scheme. FIGS. 5*a* and 5*b* illustrate an example of this aspect in which the signaling device 110 is shaped such that it has a wavy edge, and the attachment zone 120 is a wavy line printed on the outer cover 40. The user aligns the wavy edge with the wavy line to ensure proper positioning of the signaling device 110 on the absorbent article 20.

In another aspect of the present invention, the attachment zone 120 may include a full or partial schematic drawing of the signaling device 110 to provide a clear indication to the user with respect to properly positioning the signaling device 110.

In still another aspect of the present invention illustrated in FIGS. 6*a* and 6*b*, the attachment zone 120 may include a targeting graphic 125. The signaling device 110 may then be provided with a translucent portion 130 to allow a user to visually align the signaling device with the targeting graphic 125. In another aspect of the present invention, the translucent portion 130 may be a clear window. The term "translucent" generally refers to permitting the passage of light, both in the sense of being transparent, in which objects may be seen clearly therethrough, and in the sense that light may be transmitted and diffused such that objects are not seen clearly therethrough.

In yet another aspect of the present invention illustrated in FIGS. 7*a* and 7*b*, the article design scheme includes article lines 135 that may be geometric pattern, stripes, or portions of a graphic. In this aspect, the signaling device 110 also includes lines designed to align with the article lines 135 to allow a user to visually align the signaling device with the article lines 135. The lines on the signaling device 110 may a part of a pattern or graphic on the signaling device 110 or may be formed on or in the signaling device 110.

In still another aspect of the present invention illustrated in FIGS. 8a and 8b, the conductive pad members 104 and 106 or other connectors used in the absorbent article 20 may be associated with a connector graphic 140. In various aspects of the present invention, the connector graphic 140 may be any of the graphic, color, or other types described herein. In this aspect, the signaling device 110 may include similar graphics to the connector graphic 140 to provide a clear indication to the user with respect to properly positioning the signaling device 110. For example, the conductive pad member 104 or other connector may be associated with a red dot, whereas the conductive pad member 106 is associated with a blue dot. The signaling device 110 would be provided with similar red and blue dots to enable the user to align the similarly-colored dots, thus ensuring proper alignment of the signaling device 110 on the absorbent article 20.

In a further aspect of the present invention, the attachment zone 120 may include a faded portion of the article design scheme, as shown in FIGS. 4a, 4b, 9a, and 9b. The signaling device 110 would then be provided with a less faded version of the attachment zone design scheme such that attachment of the signaling device 110 to the absorbent article 20 in the proper position covers the faded attachment zone design scheme and completes the article design scheme.

In a related aspect of the present invention, the attachment zone design scheme may include a blank portion of the article design scheme as illustrated in FIGS. 2a-3b. The signaling device 110 would then be provided with the "missing" portion of the article design scheme such that attachment of the signaling device 110 to the absorbent article 20 in the proper position covers the blank attachment zone design scheme and completes the article design scheme.

In a still further aspect of the present invention illustrated in FIGS. 10a and 10b, the signaling device design scheme may include a graphic or other means of aligning the signaling device 110 with a physical aspect of the absorbent article 20. The physical aspect of the absorbent article 20 may be conductive elements 100 and/or 102, the waist region 90, the side panels 34, or any other suitable structure. For example, the conductive elements 100, 102 may be positioned such that they are visible through the outer cover 40. In another aspect of the present invention, the conductive elements 100, 102 may not be visible through the outer cover 40, but may still serve as a means for aligning signaling device 110 by feel or visual alignment. In either aspect, the signaling device design scheme may include lines or other graphics, including graphical representations of the conductive elements 100, 102 themselves, to provide a clear indication to the user with respect to properly positioning the signaling device 110 on the absorbent article 20. Alternately or additionally, the signaling device design scheme may include aspects of the shape of the case that allow the signaling device 110 to match up with the placement of the conductive elements 100, 102. For example, the signaling device case may have a small indentation, a valley, or a raised indication that is geometrically aligned with the placement of the conductive elements 100, 102 when the signaling device 110 is properly aligned.

Figure 4A:
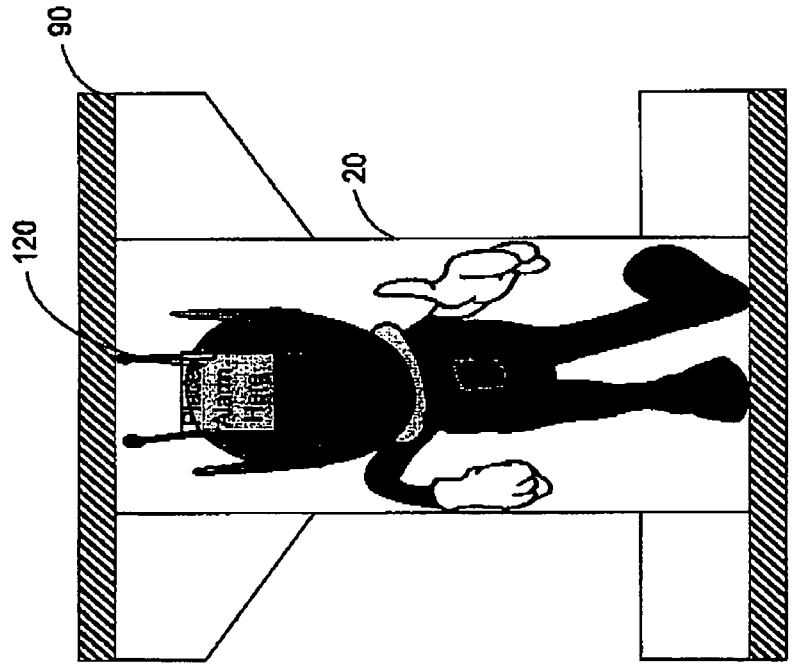
FIGS. 4a and 4b are schematic plan views of one aspect of the absorbent article illustrated in FIG. 1.
Figure 4B:
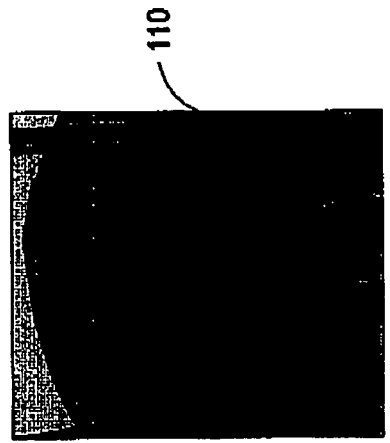

In various other aspects of the present invention, the attachment zone 120 may include any suitable combination of the graphics or other alignment aids described herein. For example, as illustrated in FIGS. 4a and 4b, the attachment zone design scheme may include a faded portion of the article design scheme, text, and an outline of the shape of the signaling device 110 to provide a clear indication to the user with respect to properly positioning the signaling device 110 on the absorbent article 20.

Figure 11A:
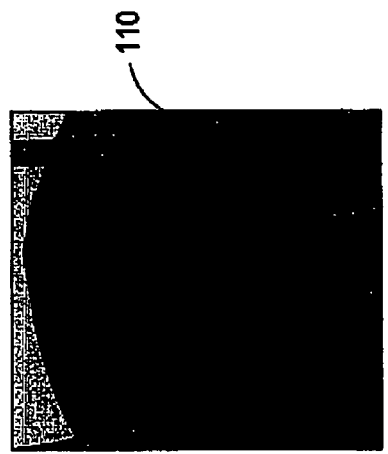
FIGS. 11a and 11b are schematic plan views of one aspect of the absorbent article illustrated in FIG. 1.
Figure 11B:
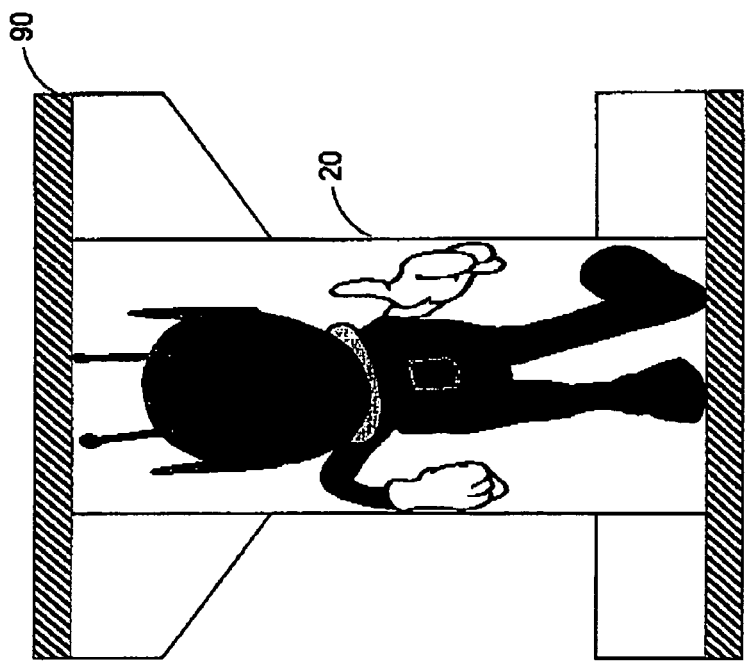

In yet another aspect of the present invention shown in FIGS. 11a and 11b, the attachment zone 120 may not be differentiated in its design, and the signaling device design scheme simply matches a portion of the article design scheme whereby attaching the signaling device 110 to the absorbent article 20 covers a portion of the article design scheme with an identical or nearly identical design on the signaling device 110.

In addition to the aspects described above, the signaling device 110 may also be provided with a means for signaling the caregiver that the signaling device 110 is properly connected to the absorbent article 20, including a confirmatory visual or auditory signal when the signaling device 110 is properly connected. Further discussion on these aspects is provided in co-pending and co-assigned U.S. patent application Ser. No. 11/412,351, filed on Apr. 26, 2006 by Long et al. and titled "Wetness Monitoring Systems With Status Notification System"; and Ser. No. 11/412,364, filed on Apr. 26, 2006 by Long et al. and titled "Wetness Monitoring Systems With Power Management"; which are incorporated herein by reference to the extent they are consistent (i.e., not in conflict) herewith.

To optimize interest and thus increase the efficacy of using the absorbent article 20 with the signaling device 110, the article design scheme, the attachment zone design scheme, and the signaling device design scheme can be coordinated in the various manners themes are described in co-pending and co-assigned U.S. patent application Ser. No. 11/414,031, filed Apr. 27, 2006 by Weber, et al. and titled "Absorbent Article with Integrated Themes," which is incorporated herein by reference to the extent it is consistent (i.e., not in conflict) herewith. In addition, the various design schemes can be coordinated with a packaging design scheme, an information design scheme, and a receiver design scheme in the various manners themes are described in the aforementioned patent application.

Suitable graphics for any of the themes described herein may include morphics as described in co-assigned U.S. patent application Ser. No. 11/192,210, filed Jul. 28, 2005 and titled "Hygiene System," which is incorporated herein by reference to the extent it is consistent (i.e., not in conflict) herewith. These and other modifications and variations to the present invention may be practiced by those of ordinary skill in the art, without departing from the spirit and scope of the present invention, which is more particularly set forth in the appended claims. In addition, it should be understood that aspects of the various aspects of the present invention may be interchanged either in whole or in part. Furthermore, those of ordinary skill in the art will appreciate that the foregoing description is by way of example only, and is not intended to limit the invention so further described in such appended claims.

What is claimed:
1. A sensing absorbent article system comprising:
an absorbent article having a liner and an outer cover, the absorbent article including
a sensing means,
a graphic article design scheme, and
an attachment zone having an attachment zone design scheme, wherein the attachment zone design scheme is visually differentiable from the article design scheme; and a signaling device adapted to be coupled to the absorbent article in the attachment zone, wherein the signaling device has a pair of terminals and a signaling device design scheme independent of the pair of terminals, wherein the signaling device design scheme aligns with one of the article design scheme and the attachment zone design scheme when the signaling device is properly coupled to the absorbent article wherein the attachment zone design scheme includes text.

2. A sensing absorbent article system comprising:
an absorbent article having a liner and an outer cover, the absorbent article including
a sensing means,
a graphic article design scheme, and
an attachment zone having an attachment zone design scheme, wherein the attachment zone design scheme is visually differentiable from the article design scheme; and
a signaling device adapted to be coupled to the absorbent article in the attachment zone, wherein the signaling device has a pair of terminals and a signaling device design scheme independent of the pair of terminals, wherein the signaling device design scheme aligns with one of the article design scheme and the attachment zone design scheme when the signaling device is properly coupled to the absorbent article wherein the attachment zone design scheme includes a faded portion of the article design scheme.

3. A sensing absorbent article system comprising:
an absorbent article having a liner and an outer cover, the absorbent article including
a sensing means,
a graphic article design scheme, and
an attachment zone having an attachment zone design scheme, wherein the attachment zone design scheme is visually differentiable from the article design scheme; and
a signaling device adapted to be coupled to the absorbent article in the attachment zone, wherein the signaling device has a pair of terminals and a signaling device design scheme independent of the pair of terminals, wherein the signaling device design scheme aligns with one of the article design scheme and the attachment zone design scheme when the signaling device is properly coupled to the absorbent article wherein the signaling devices includes a less faded version of the attachment zone design scheme.

4. A sensing absorbent article system comprising:
an absorbent article having a liner and an outer cover, the absorbent article including
a sensing means,
a graphic article design scheme, and
an attachment zone having an attachment zone design scheme, wherein the attachment zone design scheme is visually differentiable from the article design scheme; and
a signaling device adapted to be coupled to the absorbent article in the attachment zone, wherein the signaling device has a pair of terminals and a signaling device design scheme independent of the pair of terminals, wherein the signaling device design scheme aligns with one of the article design scheme and the attachment zone design scheme when the signaling device is properly coupled to the absorbent article wherein the attachment zone design scheme includes a schematic drawing of the signaling device.

5. A sensing absorbent article system comprising:
an absorbent article having a liner and an outer cover, the absorbent article including
a sensing means,
a graphic article design scheme, and
an attachment zone having an attachment zone design scheme, wherein the attachment zone design scheme is visually differentiable from the article design scheme; and
a signaling device adapted to be coupled to the absorbent article in the attachment zone, wherein the signaling device has a pair of terminals and a signaling device design scheme independent of the pair of terminals, wherein the signaling device design scheme aligns with one of the article design scheme and the attachment zone design scheme when the signaling device is properly coupled to the absorbent article wherein the attachment zone design scheme includes a targeting graphic, and wherein the signaling device includes a translucent portion to allow a user to visually align the signaling device with the targeting graphic.

6. A sensing absorbent article system comprising:
an absorbent article having a liner and an outer cover, the absorbent article including a portion of a graphic visual characteristic; and
a signaling device adapted to connect with the absorbent article, the signaling device having another portion of the graphic visual characteristic, wherein signaling device when properly aligned with the absorbent article forms a complete graphic visual characteristic.

7. An absorbent article comprising a sensing component; a liner; and an outer cover, wherein the outer cover includes a graphic visual characteristic, wherein a portion of the graphic visual characteristic is missing, and wherein the missing portion is shaped and sized to match at least a portion of a shape or a size of a signaling device adapted to be coupled to the absorbent article at the missing portion.

8. The absorbent article of claim 7, wherein the missing portion is an attachment zone adapted to indicate the proper position for a signaling device to be connected to the absorbent article.

9. A sensing absorbent article system comprising:
an absorbent article having a liner and an outer cover, the absorbent article including a conductive element; and
a signaling device adapted to connect with the absorbent article, the signaling device having a size, a shape, a pair of terminals and a signaling device design scheme independent of the size and shape of the signaling device and of the pair of terminals, wherein the signaling device design scheme is adapted to align with the conductive element.

* * * * *